United States Patent
Nakao et al.

(10) Patent No.: US 8,618,506 B2
(45) Date of Patent: Dec. 31, 2013

(54) FLUORESCENCE LIFE MEASURING APPARATUS, FLUORESCENCE LIFE MEASURING METHOD AND PROGRAM

(75) Inventors: Isamu Nakao, Tokyo (JP); Koshi Tamamura, Tokyo (JP)

(73) Assignee: Sony Corporation, Tokyo (JP)

( * ) Notice: Subject to any disclaimer, the term of this patent is extended or adjusted under 35 U.S.C. 154(b) by 257 days.

(21) Appl. No.: 13/143,518

(22) PCT Filed: Jan. 7, 2010

(86) PCT No.: PCT/JP2010/050364
§ 371 (c)(1),
(2), (4) Date: Jul. 6, 2011

(87) PCT Pub. No.: WO2010/082611
PCT Pub. Date: Jul. 22, 2010

(65) Prior Publication Data
US 2011/0266458 A1 Nov. 3, 2011

(30) Foreign Application Priority Data
Jan. 16, 2009 (JP) ................................ 2009-007722

(51) Int. Cl.
*G01J 1/58* (2006.01)
*G01N 21/64* (2006.01)

(52) U.S. Cl.
USPC ............... 250/458.1; 250/461.1; 250/459.1

(58) Field of Classification Search
USPC ............................................ 250/458.1–461.1
See application file for complete search history.

(56) References Cited

U.S. PATENT DOCUMENTS

| 4,778,763 A | 10/1988 | Makiguchi et al. |
| 6,563,584 B1 | 5/2003 | Yurino et al. |
| 2001/0055114 A1 | 12/2001 | Suzuki et al. |
| 2005/0157292 A1* | 7/2005 | Saitoh et al. ................... 356/318 |
| 2007/0026532 A1* | 2/2007 | Ikami ............................. 436/172 |
| 2010/0214632 A1* | 8/2010 | Ikari et al. ..................... 358/475 |

FOREIGN PATENT DOCUMENTS

| JP | 61 241639 | 10/1986 |
| JP | 6 3461 | 1/1994 |
| JP | 2000 304698 | 11/2000 |
| JP | 2000 321206 | 11/2000 |
| JP | 2001 349833 | 12/2001 |
| JP | 2007 33170 | 2/2007 |

OTHER PUBLICATIONS

International Search Report issued Mar. 9, 2010 in PCT/JP10/50364 filed Jan. 7, 2010.

* cited by examiner

*Primary Examiner* — David Porta
*Assistant Examiner* — Jeremy S Valentiner
(74) *Attorney, Agent, or Firm* — Oblon, Spivak, McClelland, Maier & Neustadt, L.L.P.

(57) ABSTRACT

A fluorescence life measuring apparatus, a fluorescence life measuring method and a program are described that can obtain fluorescence life using a simple configuration. The apparatus moves a stage on which a fluorescent material to be measured is placed, irradiates with excitation light the fluorescent material placed on the stage moved at a constant speed, images afterglow of emitted fluorescence caused by the excitation light, and uses an imaged image to detect the elapsed time from a fluorescence position and afterglow strength at a target afterglow position and calculate the fluorescence life.

5 Claims, 6 Drawing Sheets

FLUORESCENCE LIFE MEASURING APPARATUS, FLUORESCENCE LIFE MEASURING METHOD AND PROGRAM

TECHNICAL FIELD

The present invention relates to a fluorescence life measuring apparatus, a fluorescence life measuring method and a program, which is useful in a field in which a technique of detecting the life of emitted light caused by irradiation of excitation light is used.

BACKGROUND ART

Conventionally, a fluorescence life measuring apparatus has been proposed that irradiates a specimen supported in a cell with pulsed excitation light, measures the time waveform of emitted fluorescence caused by the excitation light using a photomultiplier tube or streak camera, and obtains the fluorescence life from the measurement result (for example, see Patent Document 1).

PRIOR ART DOCUMENT

Patent Document 1 JP-A-2001-349833

SUMMARY OF THE INVENTION

However, the photomultiplier tube or streak camera is relatively large itself, which makes such a fluorescence life measuring apparatus large as a whole. Also, in this fluorescence life measuring apparatus, a light source for irradiating with pulsed excitation light is used, and the photomultiplier tube or streak camera needs to be driven according to the timing of irradiation from the light source, which requires complicated and time-consuming adjustment process of the photomultiplier tube or streak camera.

In view of the above, the invention proposes a fluorescence life measuring apparatus, a fluorescence life measuring method and a program that can obtain fluorescence life using a simple configuration.

In order to solve the above problems, the invention provides a fluorescence life measuring apparatus including: a moving means for moving a stage on which a fluorescent material to be measured is placed; an irradiating means for irradiating with excitation light the fluorescent material placed on the stage moved at a constant speed by the moving means; an imaging means for imaging afterglow of emitted fluorescence caused by the excitation light; and a fluorescence life calculating means for using an image imaged by the imaging unit to detect the elapsed time from a fluorescence position and afterglow strength at a target afterglow position and calculate the fluorescence life.

Also, the invention provides a fluorescence life measuring method including: a moving control step of moving a stage on which a fluorescent material to be measured is placed; an irradiating step of irradiating with excitation light the fluorescent material placed on the stage moved at a constant speed through the control in the moving control step; an imaging step of imaging afterglow of emitted fluorescence caused by the excitation light; and a fluorescence life calculating step of using an image imaged in the imaging step to detect the elapsed time from a fluorescence position and afterglow strength at a target afterglow position and calculate the fluorescence life.

Also, the invention provides a program for causing: a moving control means to move a stage on which a fluorescent material to be measured is placed; an irradiating means to irradiate with excitation light the fluorescent material placed on the stage moved at a constant speed by the moving control means; an imaging means to image afterglow of emitted fluorescence caused by the excitation light; and a calculating unit to use an image imaged by the imaging means to detect the elapsed time from a fluorescence position and afterglow strength at a target afterglow position and calculate the fluorescence life.

According to the invention, the fluorescence life measuring apparatus captures the fluorescence life in the form of an afterglow image in the moving direction, which allows obtaining of the strength change of light occurring in a short period with a common camera rather than a photomultiplier tube or streak camera, resulting in a simple configuration of the fluorescence life.

MODE FOR CARRYING OUT THE INVENTION

An embodiments in accordance with the invention is described below. The description is made in the following order:
<1. Embodiment>;
[1-1. Configuration of fluorescence life measuring apparatus];
[1-2. Specific configuration of measuring unit];
[1-3. Fluorescence life measuring process];
[1-4. Effect etc.]; and
<2. Other embodiment>.

1. Embodiment

Figure 1:
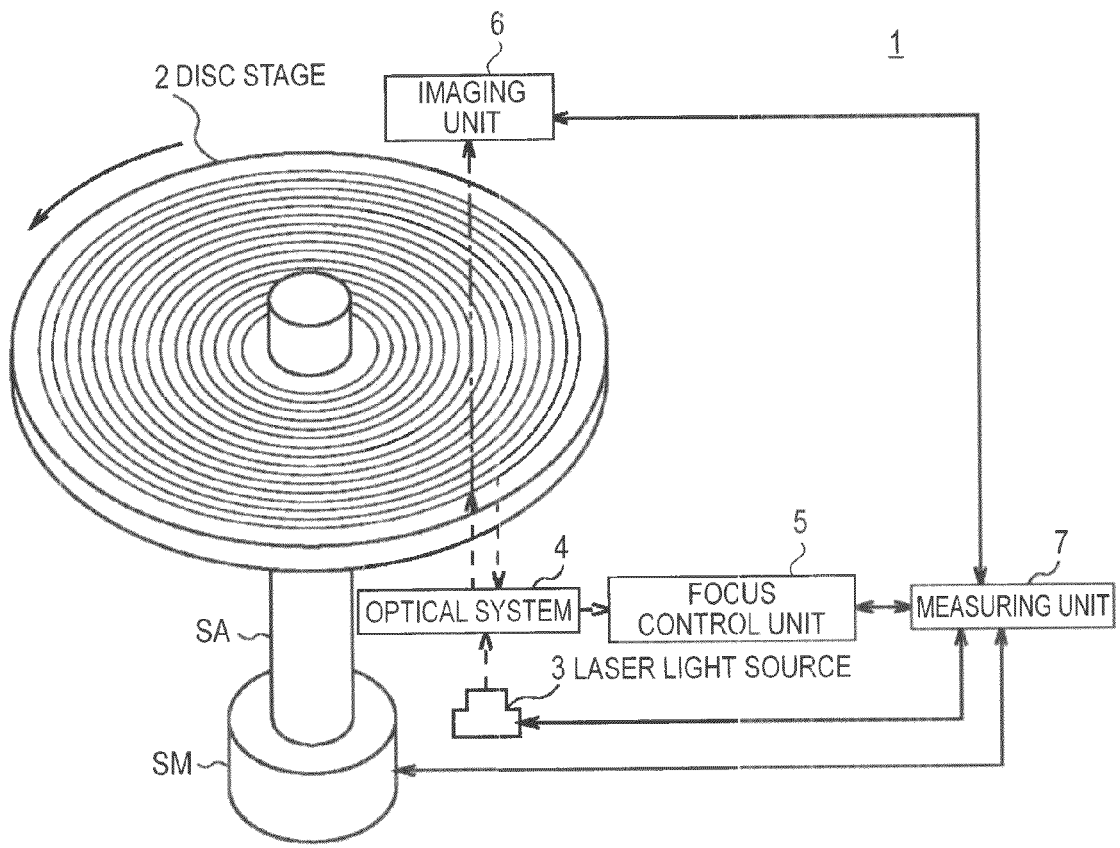
FIG. 1 schematically shows a configuration of a fluorescence life measuring apparatus.

As an embodiment in accordance with the invention, a fluorescence life measuring apparatus is described.
[1-1. Configuration of Fluorescence Life Measuring Apparatus]
FIG. 1 shows a schematic configuration of a fluorescence life measuring apparatus 1. The fluorescence life measuring apparatus 1 includes a disc-like stage (hereinafter referred to as "disc stage") 2, a laser light source 3, an optical system 4, a focus control unit 5, an imaging unit 6 and a measuring unit 7.

Figure 2:
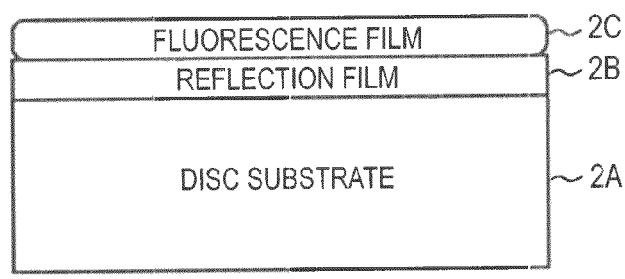
FIG. 2 schematically shows a structure of a disc stage.

The disc stage 2 is detachably supported on a rotating shaft SA through a through hole provided at the center of the disc stage 2. FIG. 2 shows a structure of the disc stage 2. The disc stage 2 has a layer structure in which a reflection film 2B and a fluorescence film 2C are formed in this order on one surface of a disc substrate 2A.

The disc substrate 2A is formed of a material that becomes transparent when irradiated with light to excite the fluorescence film 2C (hereinafter referred to as "excitation light") and has a thickness of, for example, about 1.3 mm. Specifically, quartz is used as the material, for example.

The reflection film 2B is formed of a material that can cause a predetermined amount of interface reflection and has a uniform thickness of, for example, about 100 nm. Specifically, titanium oxide is used as the material, for example, which causes about 20% of interface reflection when the excitation light has a wavelength of 405 nm and the disc substrate 2A is formed of quartz.

The fluorescence film 2C is formed of an organic or inorganic material as a target of fluorescence life measurement and has a uniform thickness of, for example, about 100 nm.

The laser light source 3 is positioned facing the surface of the disc substrate 2A other than the surface on which the reflection film 2B is formed and is configured to irradiate the fluorescence film 2C with the excitation light. The laser light source 3 used in this embodiment irradiates with the excitation light having a wavelength of 405 nm, an output power of 1 mW and a lateral mode of TEM00.

Figure 3:
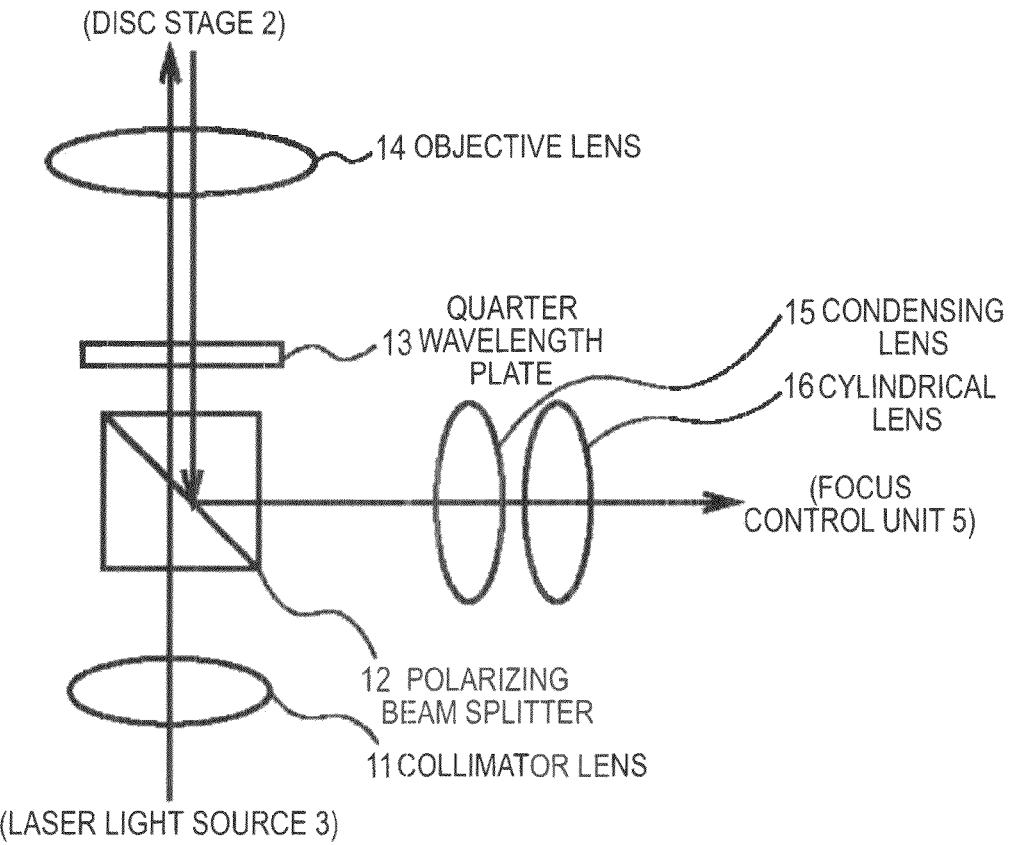
FIG. 3 shows a configuration example of an optical system.

The optical system 4 is configured to collect the excitation light irradiated by the laser light source 3 onto the interface between the disc substrate 2A and the reflection film 2B and guide the light reflected from the interface to the focus control unit 5. FIG. 3 shows a specific configuration example of the optical system 4.

In the optical system 4, laser light emitted from the laser light source 3 as linearly polarized light parallel to the plane of paper is converted into parallel light by a collimator lens 11 and guided to a polarizing beam splitter 12. Then, in the optical system 4, laser light having passed through the polarizing beam splitter 12 is converted to circularly polarized light by a quarter wavelength plate 13 and collected onto the interface between the disc substrate 2A and the reflection film 2B by an objective lens 14.

When the excitation light passes through the reflection film 2B and reaches the fluorescence film 2C, the fluorescent material to be measured, formed as the fluorescence film 2C, is excited to emit fluorescence spatially isotropically.

Also in the optical system 4, light reflected from the interface between the disc substrate 2A and the reflection film 2B is guided through the objective lens 14 to the quarter wavelength plate 13 and converted to s-polarized light by the quarter wavelength plate 13. Then, in the optical system 4, the reflected light converted to s-polarized light is reflected by 90° from the polarizing beam splitter 12 and guided through a condensing lens 15 and a cylindrical lens 16 to the focus control unit 5 (FIG. 1).

Figure 4:
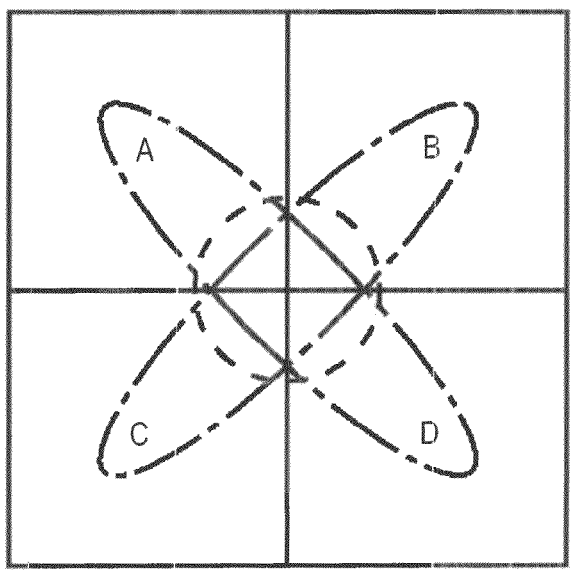
FIG. 4 schematically shows a beam shape on a light receiving surface.

The focus control unit 5 includes a light receiving unit for receiving light guided from the optical system 4. Here, FIG. 4 shows the shape of light guided from the optical system 4 on the light receiving surface of the light receiving unit. When the focus is on the interface between the disc substrate 2A and the reflection film 2B, the shape of light is circular as shown by broken line. On the other hand, when the focus is off the interface, the shape of light is elliptical as shown by alternate long and short dash line, due to aberration occurring in the cylindrical lens 16. Specifically, the long axis and short axis of the elliptical shape alternate depending on whether the focus is short of or beyond the interface between the disc substrate 2A and the reflection film 2B.

The focus control unit 5 generates focus control signal from the signal obtained from the light receiving unit as a result of photoelectric conversion in each of divided four regions. Specifically, in the example shown in FIG. 4, signals of the regions A to D are obtained, then (A+D)−(B+C) is calculated to generate the focus control signal.

The focus control unit 5 controls an actuator that can move in the optical axis direction according to the focus control signal to move the objective lens 14 (FIG. 3) provided on the actuator so that the focus is positioned on the interface between the disc substrate 2A and the reflection film 2B.

The imaging unit 6 is provided opposite the fluorescence film 2C of the disc stage 2 and is configured to image fluorescence emitted from the fluorescence film 2C and give the imaging result to the measuring unit 7 as imaging data.

The measuring unit 7 is configured to calculate fluorescence life based on the imaging data given by the imaging unit 6.

[1-2. Specific Configuration of Measuring Unit]

Figure 5:
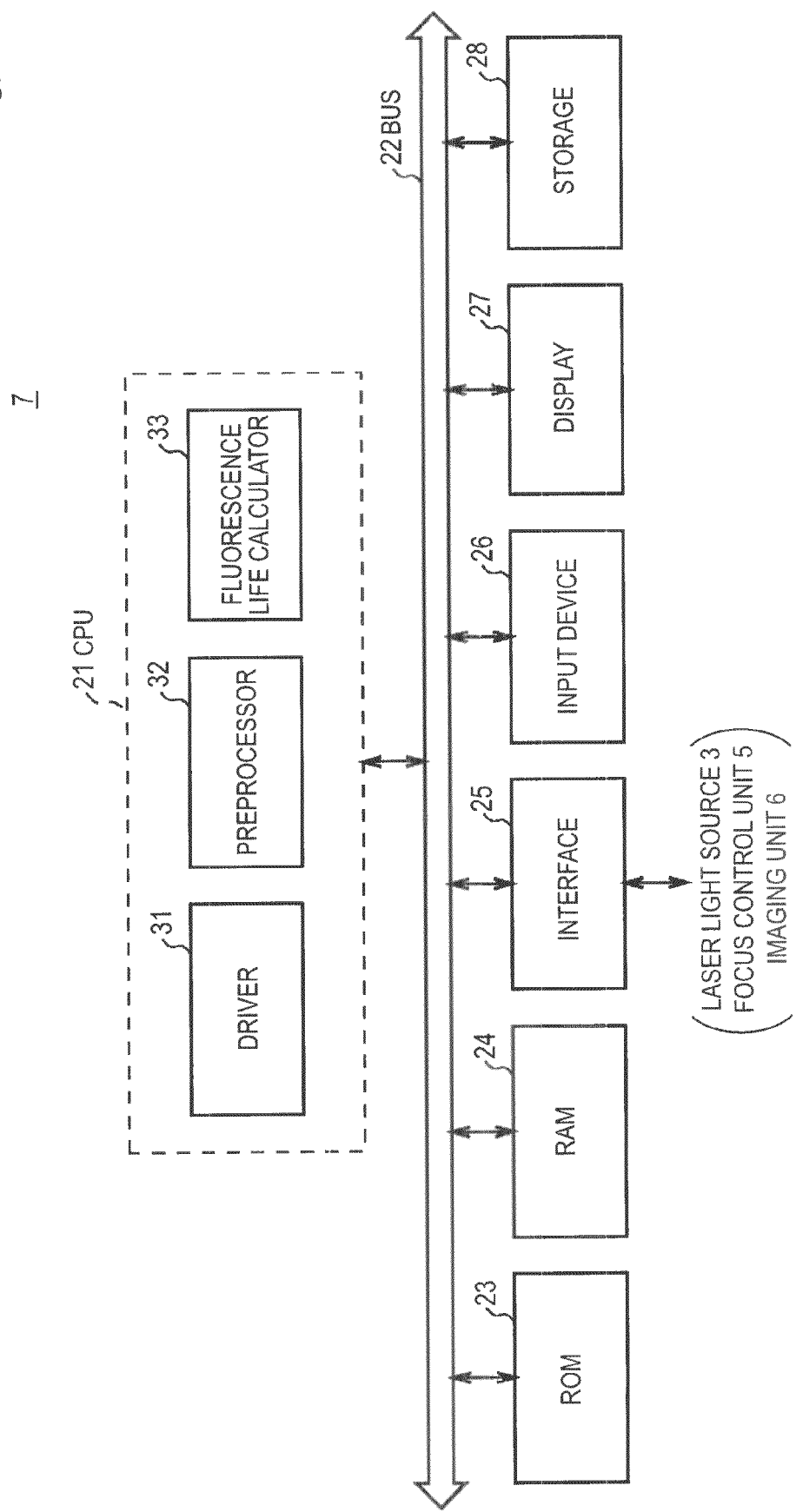
FIG. 5 is a block diagram showing a configuration of a measuring unit.

Next, the measuring unit 7 is specifically described. FIG. 5 shows a schematic configuration of the measuring unit 7. The measuring unit 7 is configured such that various hardware devices are connected to a CPU (Central Processing Unit) 21 via a bus 22.

The measuring unit 7 includes, as the hardware devices, at least a ROM (Read Only Memory) 23, a RAM (Random Access Memory) 24 as work memory of the CPU 21 and an interface 25. In this embodiment, the measuring unit 7 also includes an input device 26 for inputting an instruction according to a user operation, a display 27 and a storage 28.

The ROM 23 stores a program for performing fluorescence life measuring process (hereinafter referred to as "fluorescence life measuring program"). The interface 25 is connected to a spindle motor SM attached to the rotating shaft SA (FIG. 1), the laser light source 3, the focus control unit 5 and the imaging unit 6 (FIG. 1).

When an instruction to measure the fluorescence life is given from the operation input device, the CPU 21 expands in the RAM 24 the fluorescence life measuring program stored in the ROM 23 and functions as a driver 31, a preprocessor 32 and a fluorescence life calculator 33.

The driver 31 drives the laser light source 3 to irradiate with the excitation light in a predetermined period and drives the focus control unit 5 so that the focus is positioned on the interface between the disc substrate 2A and the reflection film 2B. Further, the driver 31 drives the spindle motor SM to rotate at a constant linear speed and drives the imaging unit 6 to image in a predetermined period.

Figure 6:
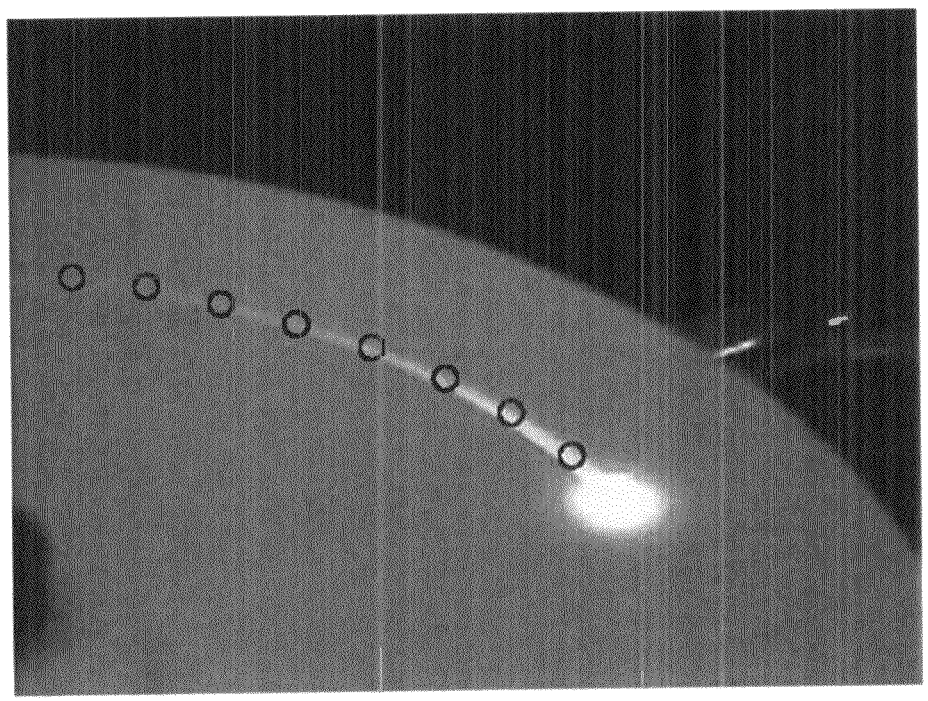
FIG. 6 is a photograph of an imaging result when excitation light is irradiated.

Here, FIG. 6 shows an imaging result of momentarily irradiating with the excitation light a predetermined position on the interface between the fluorescence disc substrate 2A and the reflection film 2B when the rotating disc stage 2 is at a position to be irradiated. Note that, in FIG. 6, a 14-bit digital still camera is used as the imaging unit 6, which includes a lens with a focal length of 6.33 to 19 mm and an 8.1 million pixel interlaced 1/2.5-inch CCD (Charge Coupled Device).

As seen from FIG. 6, when the fluorescence film 2C of the rotating disc stage 2 is momentarily excited at the irradiated position, fluorescence emitted at the irradiated position is imaged as an afterglow in the rotation direction.

The preprocessor 32 calculates the ratio of the strength at the tail position (the black circle area farthermost from the irradiated position in FIG. 6) to that at the head position (the black circle area nearest to the irradiated position in FIG. 6) of the afterglow of the fluorescence emitted at the irradiated position in an image represented by the imaging data given by the imaging unit 6.

Then, the preprocessor 32 adjusts the rotation speed of the disc stage 2 or the angle of view of the imaging unit 6 through the interface 25 so that the ratio falls within a defined range. Consequently, the afterglow from the irradiated position to a position at which a target strength is maintained (for example, a position just before disappearance) falls within the imaging range.

Figure 7:
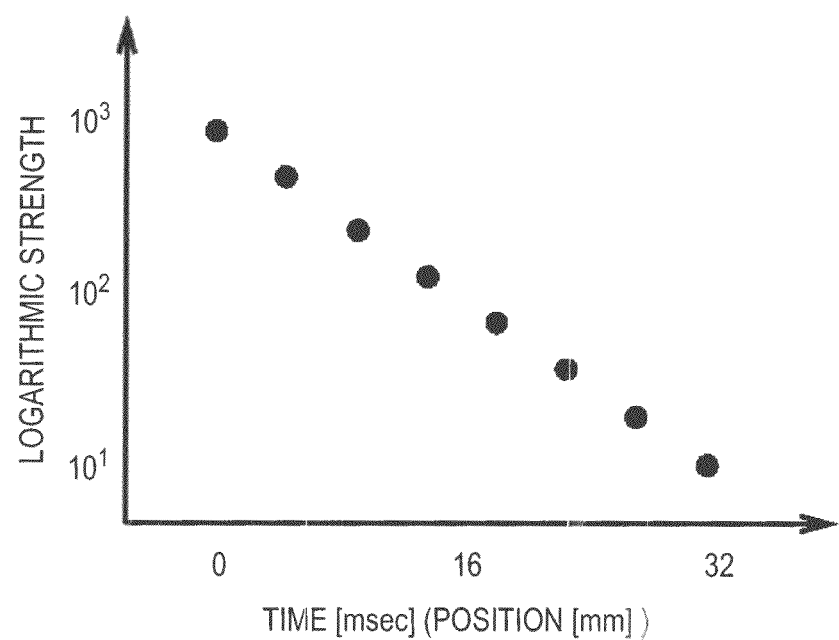
FIG. 7 is a graph showing afterglow strength change over time.

When the rotation speed of the disc stage 2 or the angle of view of the imaging unit 6 has been adjusted, the fluorescence life calculator 33 calculates the strength and elapsed time of the afterglow from the head position to the tail position at predetermined intervals (at black circles in FIG. 6) and creates a table showing the change of the afterglow over time (hereinafter referred to as "afterglow change table") based on the calculation result. FIG. 7 shows the afterglow change table for the afterglow shown in FIG. 6.

The elapsed time can be determined from the position information of the afterglow and the radius and rotation speed of the disc stage.

Then, the fluorescence life calculator 33 calculates the fluorescence life based on the following equation:

$$I_{(t)} = I_0 \cdot \exp(-t/T) \quad (1)$$

where $I_{(t)}$ is the afterglow strength at the positions to be noted (afterglow strength change over time), $I_0$ is the strength at the irradiated position, t is the elapsed time at the positions to be noted, and T is the fluorescence life. Further, $-t/T$ means the gradient of the afterglow change table (FIG. 6).

By the way, the fluorescence film 2C (FIG. 2) formed on the disc stage 2 is not limited to have a single excitation state, but may have multiple excitation states. When the fluorescence film 2C has multiple excitation states, the afterglow change table does not show a linear relationship as shown in FIG. 7, but shows a mixture of multiple linear relationships depending on the number of the excitation states.

In this case, the fluorescence life calculator 33 can calculate the fluorescence life of the fluorescence film 2C having multiple excitation states by designating linear portions having different gradients and curved portions of the slope in the afterglow change table as positions to be noted.

For the fluorescence film 2C presenting the slope shown in FIG. 6, the fluorescence life is calculated to be 1.8 msec when the linear speed of the disc stage 2 in imaging shown in FIG. 5 is 1 m/sec.

[1-3. Fluorescence Life Measuring Process]

Figure 8:
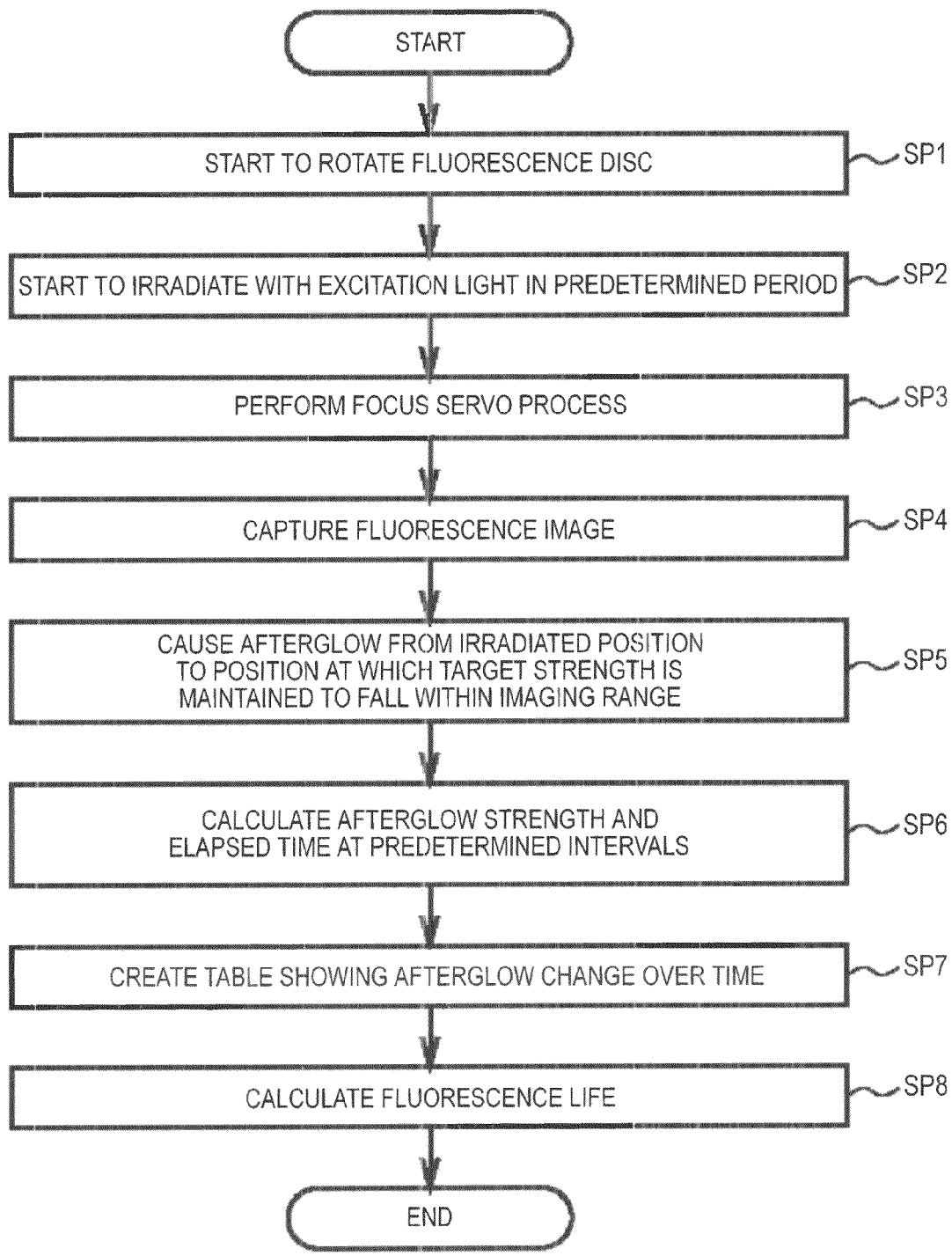
FIG. 8 is a flowchart showing a fluorescence life measuring process.

Next, a fluorescence life measuring process of the measuring unit 7 is described with reference to a flowchart shown in FIG. 8.

When an instruction to measure the fluorescence life is given, the CPU 21 starts the fluorescence life measuring process to proceed to a first step SP1. In the first step SP1, the CPU 21 drives the spindle motor SM to rotate the disc stage 2 at a constant linear speed, then proceeds to a second step SP2.

In the second step SP2, the CPU 21 drives the laser light source 3 to irradiate the disc stage 2 with the excitation light in a predetermined period, then proceeds to a third step SP3. In the third step SP3, the CPU 21 drives the focus control unit 4 to position the focus on the interface between the disc substrate 2A and the reflection film 2B, then proceeds to a fourth step SP4.

In the fourth step SP4, the CPU 21 drives the imaging unit 6 to start capturing an image at the time of irradiating the disc stage 2 with the excitation light, then proceeds to a fifth step SP5.

In the fifth step SP5, the CPU 21 causes the afterglow from the irradiated position to a position at which a target strength is maintained (for example, a position just before disappearance) of the image captured in the fourth step SP4 to fall within the imaging range, then proceeds to a sixth step SP6. Specifically, as described above, the rotation speed of the disc stage 2 or the angle of view of the imaging unit 6 is adjusted so that the ratio of the strength at the tail position to that at the head position of the afterglow of the fluorescence emitted at the irradiated position falls within a defined range.

In the sixth step SP6, the CPU 21 calculates the strength and elapsed time of the afterglow from the head position to the tail position at predetermined intervals, then proceeds to a seventh step SP7. In the seventh step SP7, the CPU 21 creates an afterglow change table based on the calculation result of the sixth step SP6, then proceeds to an eighth step SP8.

In the eighth step SP8, the CPU 21 calculates the fluorescence life based on the equation (1), then ends the fluorescence life measuring process. Note that the CPU 21 is configured so that, when the slope created in the seventh step SP7 is nonlinear, the CPU 21 calculates the fluorescence life for each of linear portions having different gradients and curved portions of the slope shown in the afterglow change table in the eighth step SP8.

[1-4. Effect Etc.]

In the above configuration, the fluorescence life measuring apparatus 1 irradiates a fluorescent material placed on the rotating disc stage 2 with excitation light and images afterglow of emitted fluorescence caused by the excitation light in the imaging unit 6. Then, the fluorescence life measuring apparatus 1 detects the elapsed time from a fluorescence position and afterglow strength at a target afterglow position and calculates the fluorescence life from the afterglow strength and elapsed time.

The fluorescence life measuring apparatus 1 captures the fluorescence life in the form of an afterglow image in the rotation direction, which allows obtaining of the strength change of light occurring in a short period without using a streak camera, resulting in a simple configuration of the fluorescence life.

Furthermore, the fluorescence life measuring apparatus 1 momentarily irradiates the fluorescent material placed on the rotating disc stage 2 with laser light at a predetermined period. Thus, the fluorescence life measuring apparatus 1 can be configured more simply than the case of using pulsed laser light. Also, the fluorescence life measuring apparatus 1 can reduce the property change of the fluorescent material caused by the excitation light in comparison with the case of continuously irradiating with pulsed laser light while measuring, which allows correctly measuring of the fluorescence life of the fluorescent material to be correctly measured.

Furthermore, when lines showing the afterglow strength change over time are nonlinear, the fluorescence life measuring apparatus 1 calculates the fluorescence life for each of linear portions having different gradients and curved portions of those lines.

Thus, even when the fluorescent material has multiple excitation states, the fluorescence life measuring apparatus 1 can calculate the fluorescence life of the fluorescent material.

According to the above configuration, the fluorescence life measuring apparatus 1 captures the fluorescence life in the form of an afterglow image in the rotation direction, which allows obtaining of the strength change of light occurring in a short period without using a streak camera, resulting in a simple configuration of the fluorescence life.

2. Other Embodiment

In the above embodiment, before calculating the fluorescence life, the rotation speed of the disc stage 2 or the angle of view of the imaging unit 6 is adjusted so that the ratio of the strength at the tail position to that at the head position of the imaged afterglow falls within a defined range.

Rather than this embodiment, the angle of view of the imaging unit 6 may be fixed so that the entire disc stage 2 falls within the imaging range. This configuration allows calculating of the fluorescence life in a way similar to the above embodiment while keeping constant the ratio of the fluorescence strength and the afterglow strength within the imaging range, without the above-described adjustment. However, in terms of afterglow sensitivity, the above embodiment in which the rotation speed of the disc stage 2 or the angle of view of the imaging unit 6 is adjusted is preferable.

Furthermore, in the above embodiment, as an moving means for moving the stage on which a fluorescent material to be measured is placed, the spindle motor SM is used to rotationally move the stage. However, the moving means is not limited to one that rotationally moves the stage. For example, one that linearly moves the stage can be used. Anyway, the moving means has only to be able to provide a constant moving speed in an entire process or a portion thereof.

Furthermore, in the above embodiment, the fluorescent material to be measured is placed on the entire disc stage 2 in the form of a film. However, the placement position is not limited to the entire stage, and further, the placement may be performed in any other form than the film.

INDUSTRIAL APPLICABILITY

The invention can be utilized in bio-based applications, such as gene testing, pharmaceutical origination or patient follow-up.

DESCRIPTION OF REFERENCE NUMERALS AND SIGNS

1 fluorescence life measuring apparatus, 2 disc stage, 2A disc substrate, 2B reflection film, 2C fluorescence film, 3 laser light source, 4 optical system, 5 focus control unit, 6 imaging unit, 7 measuring unit, 21 CPU, 22 bus, 23 ROM, 24 RAM, 31 driver, 32 preprocessor, 33 fluorescence life calculator, SM spindle motor, SA rotating shaft

The invention claimed is:

1. A fluorescence life measuring apparatus comprising:
a support structure that moves a stage on which a fluorescent material to be measured is placed;
a light source that irradiates with excitation light the fluorescent material placed on the stage moved at a constant speed by the support structure;
an imaging device that images afterglow of emitted fluorescence caused by the excitation light; and
processing circuitry that uses an image imaged by the imaging device to detect the elapsed time from a fluorescence position and afterglow strength at a target afterglow position and calculate the fluorescence life,
wherein the processing circuitry, when lines showing logarithmic afterglow strength change over time are nonlinear, calculates the fluorescence life for each of linear portions having different gradients and curved portions of those lines.

2. The fluorescence life measuring apparatus according to claim 1, wherein
the processing circuitry adjusts the moving speed of the support structure or the angle of view of the imaging device so that the ratio of the strength at the tail position to that at the head position of the imaged afterglow falls within a defined range,
and calculates the fluorescence life from the images after the adjustment is performed.

3. The fluorescence life measuring apparatus according to claim 2, wherein the support structure rotationally moves the stage on which the fluorescent material to be measured is placed.

4. A fluorescence life measuring method comprising:
a moving control step of moving a stage on which a fluorescent material to be measured is placed;
an irradiating step of irradiating with excitation light the fluorescent material placed on the stage moved at a constant speed through the control in the moving control step;
an imaging step of imaging afterglow of emitted fluorescence caused by the excitation light; and
a fluorescence life calculating step of using an image imaged in the imaging step to detect the elapsed time from a fluorescence position and afterglow strength at a target afterglow position and calculate the fluorescence life,
wherein the fluorescence life calculating step further comprising the step of, when lines showing logarithmic afterglow strength change over time are nonlinear, calculating the fluorescence life for each of linear portions having different gradients and curved portions of those lines.

5. A non-transitory computer readable storage medium including executable instructions, which when executed by a computer cause a computer to execute a method for use in an information processing apparatus including circuitry configured to implement an application execution unit, a file conversion unit, and a media interface, the method comprising the steps of:
a moving control step of moving a stage on which a fluorescent material to be measured is placed;
an irradiating step of irradiating with excitation light the fluorescent material placed on the stage moved at a constant speed through the control in the moving control step;
an imaging step of imaging afterglow of emitted fluorescence caused by the excitation light; and
a fluorescence life calculating step of using an image imaged in the imaging step to detect the elapsed time from a fluorescence position and afterglow strength at a target afterglow position and calculate the fluorescence life,
wherein the fluorescence life calculating step further comprising the step of, when lines showing logarithmic afterglow strength change over time are nonlinear, calculating the fluorescence life for each of linear portions having different gradients and curved portions of those lines.

* * * * *